(12) United States Patent
Johnson et al.

(10) Patent No.: US 7,795,863 B2
(45) Date of Patent: Sep. 14, 2010

(54) METHOD AND APPARATUS FOR FORMING COIL FOR USE IN EDDY CURRENT SENSING PROBE

(75) Inventors: Marcus James Johnson, Ames, IA (US); Norio Nakagawa, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 1144 days.

(21) Appl. No.: 11/064,325

(22) Filed: Feb. 23, 2005

(65) Prior Publication Data

US 2005/0184729 A1 Aug. 25, 2005

Related U.S. Application Data

(60) Provisional application No. 60/546,883, filed on Feb. 23, 2004.

(51) Int. Cl.
G01N 27/90 (2006.01)
(52) U.S. Cl. .................. 324/222; 324/223; 324/234; 324/238
(58) Field of Classification Search .......... 324/222, 324/233, 234, 238
See application file for complete search history.

(56) References Cited

U.S. PATENT DOCUMENTS

| | | | | |
|---|---|---|---|---|
| 3,659,240 A | * | 4/1972 | Learned et al. | 336/200 |
| 5,055,784 A | * | 10/1991 | Jaeger et al. | 324/233 |
| 5,396,698 A | * | 3/1995 | Orthmann et al. | 29/600 |
| 5,547,532 A | * | 8/1996 | Wernersbach et al. | 156/172 |
| 5,623,204 A | * | 4/1997 | Wilkerson | 324/228 |
| 5,841,277 A | | 11/1998 | Hedengren | |
| 6,004,661 A | * | 12/1999 | Sakai et al. | 428/216 |
| 6,037,768 A | | 3/2000 | Moulder | |
| 6,093,437 A | | 7/2000 | Katta | |
| 6,339,331 B1 | | 1/2002 | Ruzzo | |
| 2004/0245997 A1 | | 12/2004 | Plotnikov | |
| 2005/0093667 A1 | * | 5/2005 | Kilian et al. | 336/200 |

FOREIGN PATENT DOCUMENTS

JP 03134809 A * 6/1991

OTHER PUBLICATIONS

M³D™ Technology, "Maskless Mesoscale Materials Deposition M³D", 2003 1 page.

(Continued)

*Primary Examiner*—Reena Aurora
(74) *Attorney, Agent, or Firm*—McKee, Voorhees & Sease, P.L.C.

(57) ABSTRACT

A coil for use in an eddy current sensing probe is formed through depositing film traces. The film traces can be directly deposited. The film traces can be deposited on the outer surface of a core or on ends of the core. The film traces can be deposited onto non-planar surfaces other than cores for the inspection of parts having complex geometries. The coil can be used in a single coil probe or in a probe having a sensor array.

15 Claims, 8 Drawing Sheets

OTHER PUBLICATIONS

Gilleo, columinst, "Metalworking iin the 21st Century", Semiconductor International, Reed Electronics Group, Oct. 1, 2002, 2 pages.

King, Bruce, "Maskless Mesoscale MAterials Deposition", Semiconductor International, Reed Electronics Group, Optomec Inc., Albuquerque, N.M., Feb. 1, 2003, 4 pages.

King, et al. "$M^3D$ Technology deposits electronic materials onto low-temperature, non-planar substrates without masks or resists", Optomec, Inc., www.optomec.com, 5 pages.

$M^3D$™, Maskless Mesoscale™ Materials Deposition. Optomec, Inc., www.optomec.com, 2 pages.

* cited by examiner

METHOD AND APPARATUS FOR FORMING COIL FOR USE IN EDDY CURRENT SENSING PROBE

CROSS-REFERENCE TO RELATED APPLICATIONS

This application claims priority to U.S. Provisional Patent Application Ser. No. 60/546,883 filed Feb. 23, 2004, which is incorporated by reference herein in its entirety.

BACKGROUND OF THE INVENTION

The present invention relates to a method and apparatus for a coil. More particularly, but not exclusively, the present invention relates to an eddy current coil for use in an eddy current sensing probe.

Eddy current sensing has long been used within the field of nondestructive evaluation (NDE). Although configurations can vary, in a typical application a probe with an eddy current sensing coil is placed near an object to be tested. A coil is activated resulting in the formation of eddy currents associated with the object under test. Analysis of the resulting eddy currents can be used to detect various parameters associated with the object under test. For example, in the context of aircraft a number of flaw types and sizes can be identified, including but not limited to stress fractures in an aircraft wing, corrosion in the vicinity of a lap joint, and other conditions. One skilled in the art will recognize that eddy current sensing is used in a variety of contexts or environments, especially critical components such as air frames, engine parts, nuclear power plant tubes, etc.

Conventionally, the coils for use in an eddy current sensing probe are formed by hand. The coil is formed by turning a wire a number of times around a core. There are numerous problems associated with this handcrafting method of forming of a coil. Many of these problems stem from the imprecision of this process. Slight differences in the number of turns of the coil, the spacing between the turns of the coil, the alignment of the coil on a core, and other difficult to control variations result in variability in the resulting coils and the resulting probes. Many eddy current coils have multiple layers of turns and more than one set of windings. Very thin wire (50 AWG) is sometimes used, making manufacturing an extremely delicate operation.

This variability is seen as a significant problem in the industry. In fact, at least one study indicates that current manufacturing techniques lead to a variability in performance as high as 400%. Variability can result in difficulties in calibration, increased time to perform an analysis or evaluation, and the potential for improper analysis if the variability is not taken into consideration during the evaluation process. Therefore variability increases costs in the performance of nondestructive testing using eddy currents.

Some of the common problems encountered with eddy current probes include difficulties arising from tilt of the windings, tilt of the ferrite core, or both. Another problem is chipped or otherwise damaged ferrite cores. These factors can all effect performance and will lead to variabilities that may be hard to account for. Model-based measurement techniques, often consider to be the future of quantitative eddy-current nondestructive evaluation, may be inaccurate as a result of such variabilities.

It is further noted that wire twisted or turned within a probe body can lead to stray inductance and can also adversely affect the electrical properties of the probe. What is needed is a method to reduce variabilities due to probe internal connections.

Another problem with eddy current sensing is the amount of time required to inspect a component or surface. It would be advantageous to reduce the amount of time involved in inspecting such a component or surface.

Therefore, it is a primary object, feature, or advantage of the present invention to improve upon the state of the art by providing a method and apparatus for a coil for use in an eddy current sensing probe.

It is a further object, feature, or advantage of the present invention to provide a coil for an eddy current sensing probe that is conducive to being manufactured through automated processes.

It is a still further object, feature, or advantage of the present invention to provide a coil for use in an eddy current sensing probe that reduces manufacturing time and costs.

Another object, feature, or advantage of the present invention is a method and apparatus for a coil for an eddy current sensing probe that is not limited in size or performance by handcrafting techniques.

Yet another object, feature, or advantage of the present invention is a method and apparatus for a coil for an eddy current sensing probe that includes multiple stacked windings.

A still further object, feature, or advantage of the present invention is a method and apparatus for a coil for an eddy current sensing probe that improves accuracy by reducing the differences between models of the probe and the actual probe.

Another object, feature, or advantage of the present invention is to provide an array of coils for use in eddy current sensing.

Yet another object, feature, or advantage of the present invention is to provide an eddy current sensor configuration that allows for quickly scanning a component or surface.

A further object, feature, or advantage of the present invention is to provide a coil for use in an eddy current sensing probe that is easy to construct.

A still further object, feature, or advantage of the present invention is to provide a coil for use in eddy current sensing that allows for convenient inspection of complex parts.

Another object, feature, or advantage of the present invention is to provide a coil for use in eddy current sensing that allows for positional reproducibility in the inspection process.

Yet another object, feature, or advantage of the present invention is to provide a coil with a molded body to improve positional reproducibility associated with an inspection process.

One or more of these and/or other objects, features, or advantages of the present invention will become apparent from the specification and claims that follow.

SUMMARY OF THE INVENTION

The present invention provides a method and apparatus for a coil for use in an eddy current sensing probe. The coil described is conducive to machine manufacturing and provides for a reduction in the variability of eddy current coils.

According to one aspect of the invention, a method of forming a coil for use in any eddy current sensing probe is described. A coil body is provided that has a first end and an opposite second end. The coil body also has an outer surface extending around the coil body. A film winding is then deposited on the coil body. The film winding includes a number of turns that overlay the body. Each of the turns extends annularly around the body. The film turns can be formed in various ways including direct-writing, printing, and vapor deposition. Also, according to the method, there may be one or more insulative layers including an insulator between the body and the film windings as well as an insulator between the film linings and a return track.

According to another aspect of the present invention, a coil for use in an eddy current sensing probe is described. The coil includes a body that has a first end and an opposite second end. There is an outer surface extending around the body. A film winding has a plurality of turns overlaying the core body. The plurality of turns extends annularly around the body. There can also be one or more insulative layers overlaying the body. A first insulative layer can directly overlay and attach to the body and the film winding would then directly overlay and attach to the first insulative layer. The first insulative layer preferably provides a smooth surface on which to deposit the film windings. A second insulative layer can overlay at least a portion of the film winding. A film return track can be deposited on the second insulative layer. The coil can include a first pad and a second pad electrically connected to opposite ends of the windings.

According to another aspect of the present invention, an eddy current sensing probe is described. The eddy current sensing probe includes a probe housing and an eddy current coil disposed within the probe housing. The eddy current coil includes a core body having a first end and an opposite second end with an outer surface extending around the core body. There is also a film winding having a number of turns that overlays the core body including either extending annularly around the outer surface of the core body or on an end of the core body. The eddy current coil preferably has a pair of pads for connecting the film windings. The probe housing is preferably adapted to engage the eddy current coil. This can be performed through a press-fit fitting or a clip-type fitting. The pads are preferably releasably engaged with the probe housing to facilitate removal and replacement of the eddy current coil.

According to another aspect of the present invention a method of forming a coil for use in an eddy current sensing probe is provided. The method includes providing a body having a first end and an opposite second end, and an outer surface extending around the body. The method further includes depositing a film winding comprising a plurality of turns to overlay the body, each of the plurality of turns deposited on the first end of the body. The body can be of a substantially cylindrical shape or can be of a polyhedral shape. The film winding can be deposited in various ways, including through a direct write process. A plurality of coil patterns can be deposited on the first end. For example, two coils can be configured in a differential configuration.

According to yet another aspect of the present invention, a device for eddy current sensing is disclosed. The device includes a substrate and a plurality of eddy current sensor elements disposed on the substrate. Each of the eddy current sensor elements includes film windings deposited on the substrate. The film windings can be deposited through direct writing. The substrate is preferably a flexible substrate such as a polyimide.

DETAILED DESCRIPTION OF EXEMPLARY EMBODIMENTS

Exemplary embodiments of the present invention are now described. The present invention is not to be limited to these particular embodiments. It is to be understood that these exemplary embodiments are not to be used to limit the broad scope of the present invention and that the present invention contemplates numerous variations.

Figure 1:
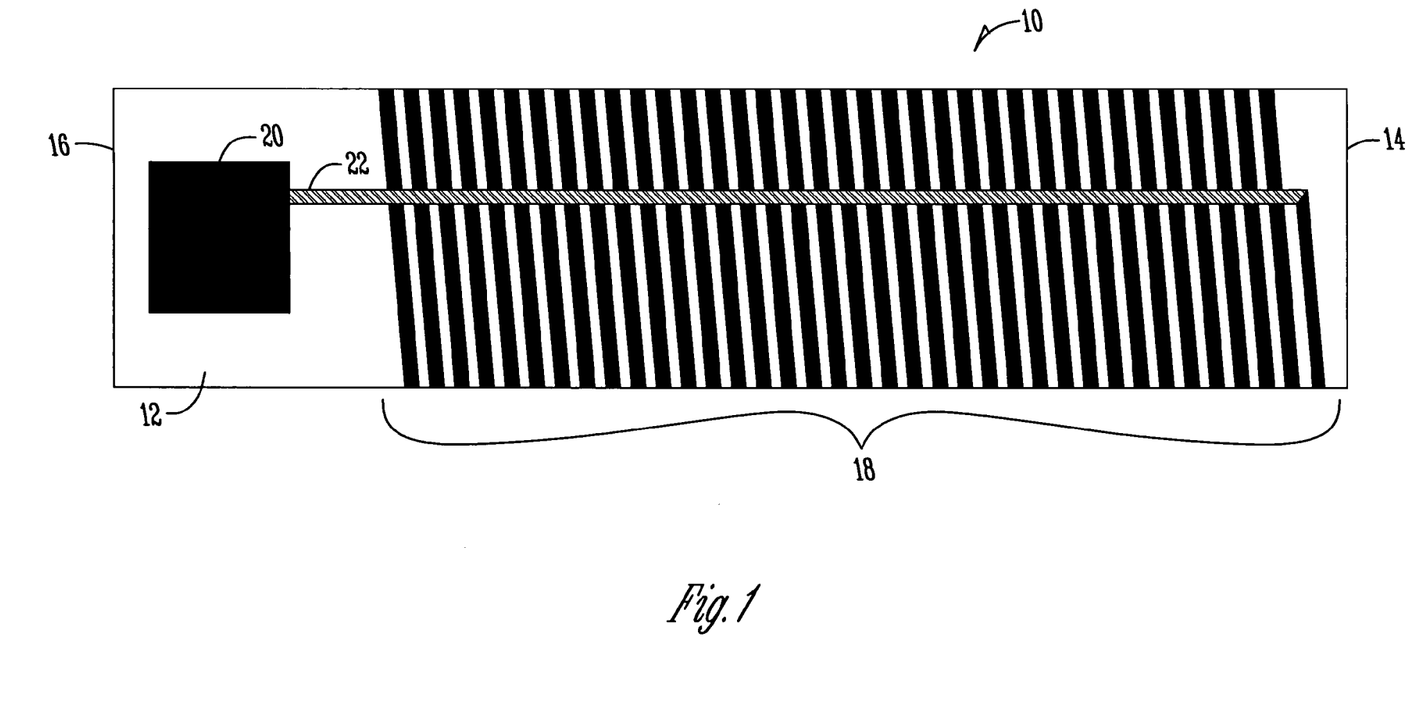
FIG. 1 is a representation of one embodiment of an eddy current coil according to the present invention.

The term "coil" is used throughout to describe an element associated with an eddy current sensing probe. One should appreciate that the term "coil" is to be given a broad definition. The term "coil" is not to be limited to a particular shape or geometry associated with prior art coils. One embodiment of an eddy current coil of the present invention is illustrated in FIG. 1. The coil 10 shown has a first end 14 and an opposite second end 16. The coil 10 as shown is of a substantially cylindrical shape with an outer surface 12. The present invention, however, contemplates the coil 10 does not necessarily need to be cylindrical in shape. For example, the core can be of other polyhedral shapes. A winding 18 is also shown. The winding 18 is comprised of a number of turns. The winding 18 is a film winding 18. Note the consistency in the spacing between each turn of the winding 18 and the consistency in the width of each turn of the coil. The present invention provides a level of precision that is difficult to obtain by hand winding wire around a core particular when forming small windings. A pad 20 is shown for connecting the coil 10 to a wire lead or otherwise to another electrical connection within a probe housing. A return trace 22 is shown that connects one end of the winding to the pad 20. The return trace 22 is insulated from the other turns of the winding 18.

A methodology of forming the coil of FIG. 1 is now described. According to the methodology, a core is provided.

Figure 2:
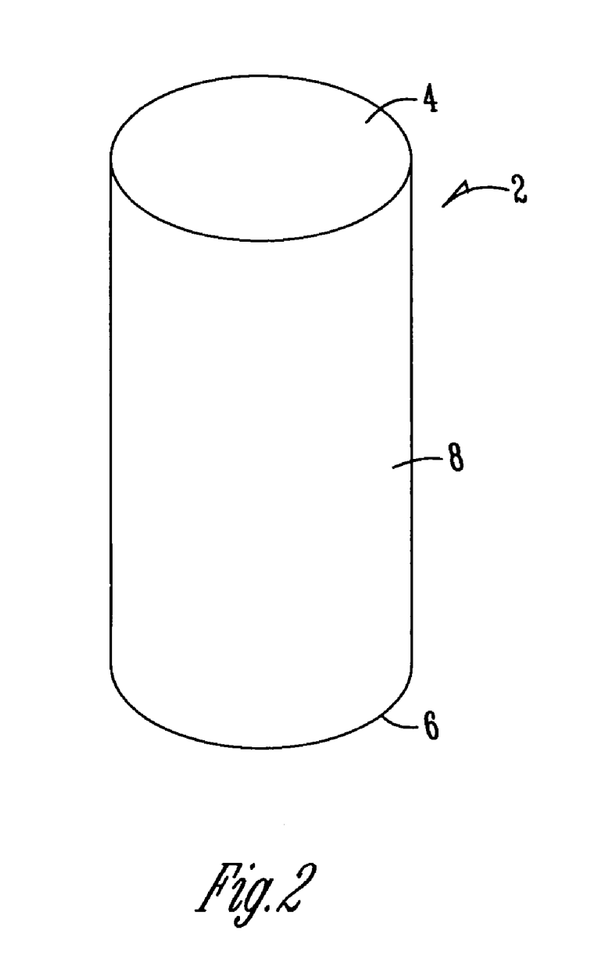
FIG. 2 illustrates one embodiment of an eddy current sensing probe according to the present invention.

FIG. 2 illustrates one embodiment of a core 2. The core 2 can be comprised of a ferrite material or can be plastic or other material. The core 2 has a first end 4 and an opposite second end 6. There is an outer surface 8 between the first end 4 and the second end 6. The core 2 is preferably in a substantially cylindrical shape as shown, but need not be. The core can be of other polyhedral shapes as may be appropriate in a particular application. The core 2 can be of a number of shapes that allow windings to be deposited on it.

Figure 3:
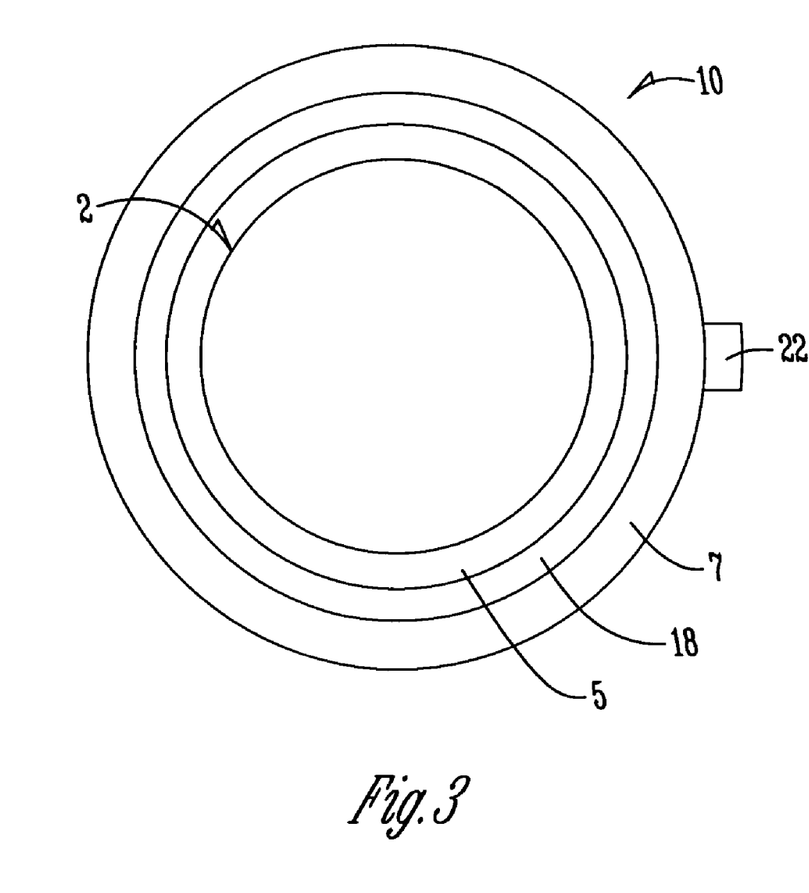
FIG. 3 illustrates one embodiment of an interface between pads of a eddy current coil and the probe housing.

FIG. 3 illustrates a cross-section of the coil to aid in the explanation of the methodology of forming a coil. It should be appreciated that the various layers shown in FIG. 3 are not to scale. FIG. 3 is simply provided as an aid to explanation of the various layers of the coil 10. In FIG. 3, the core 2 is preferably ferrite. One of the problems with ferrite is that the surface of the ferrite is not smooth and therefore presents difficulties if film windings were to be deposited directly upon it. Therefore, in FIG. 3, an insulative layer 5 is applied to the ferrite core 2. The insulative layer 5 can be, but need not be, a plastic such as a thermoplastic polymer-like polyurethane. Polyurethane coating acts as an electrical insulator and also provides a smooth surface. The present invention contemplates that where the insulative layer is needed, any number of types of materials can be used and the layer can be deposited in any number of ways. This includes depositing the insulative layer via the direct write process described below with respect to the film windings. Where used, the insulative layer preferably provides a smooth surface for the deposit of a film winding 18. The film winding 18 can be deposited in various ways. One method that can be used is to use an instrument from Optomec. This type of technology is essentially direct-writing a thin track onto a substrate. The Optomec technology allows a thin track of as little as 10 micrometers to be deposited. The present invention, however, contemplates that other types of deposition techniques can be used, including printing, vapor deposit techniques, and other types of techniques. Another example of a technique that can be used is to deposit the windings and then ablate unwanted material such as through laser ablation. The present invention is not to be limited to the particular deposition technique used whether additive (such as direct write) or substractive (such as laser ablation). It should be appreciated, however, that whatever technique is used, the technique needs to be capable of operation in conjunction with the outer surface of the present invention where the outer surface can be cylindrical in nature or otherwise polyhedral as opposed to merely being a flat surface.

It should be further appreciated that the present invention contemplates that the width of the track of the winding can vary. Although it need not be, the width can be smaller than what is realizable by hand winding. The present invention further contemplates that multiple stacked windings can be used.

It should be appreciated that in this direct-write embodiment, the windings of the coil are deposited or "written" and there needs to be some point of connection between the end of the coil and the end of the body where the writing begins. Therefore, a second insulative layer 7 is deposited over the winding 18. Then, a return path 22 can be written. The return path 22 is culminated in a pad. Referring back to FIG. 1, the pad 20 is shown electrically connected to the return path 22. The return path 22 connects to the end of a winding. There is a coating of an insulative material between the winding 18 and the return path 22. A second pad (not shown) is preferably positioned on the opposite side of the coil 10, and is connected to the opposite end of the winding.

It should be understood that the present invention contemplates numerous variations, including the types of materials used. It should also be apparent that the first insulative layer need not be used if the core is conducive to having the film windings deposited on it, i.e. it is sufficiently smooth and non-conductive. The present invention further contemplates that various types of metal or other conductor can be used for the windings and the various parts can be of various sizes.

Figure 4:
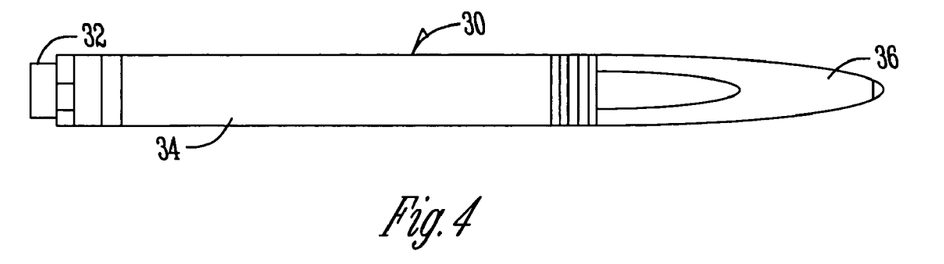
FIG. 4 is a view of one embodiment of the present invention showing an eddy current sensing probe.

FIG. 4 illustrates one embodiment of an eddy current sensing probe 30 according to the present invention. The probe 30 includes a probe housing 34. There is a probe connector 32 on one end of the probe 30. The probe connector 32 can be a coaxial-type connection or other type of connection. On the opposite end of the probe housing 34 is the probe tip 36. A coil is disposed within the probe housing proximate the probe tip 36. Leads within the probe housing 34 will then extend from the coil to the connector 32. Although a pencil-type probe 30 is shown in FIG. 4, it should be appreciated that the present invention contemplates numerous configurations of eddy current sensing probes and is in no way limited to that which is shown.

Figure 5:
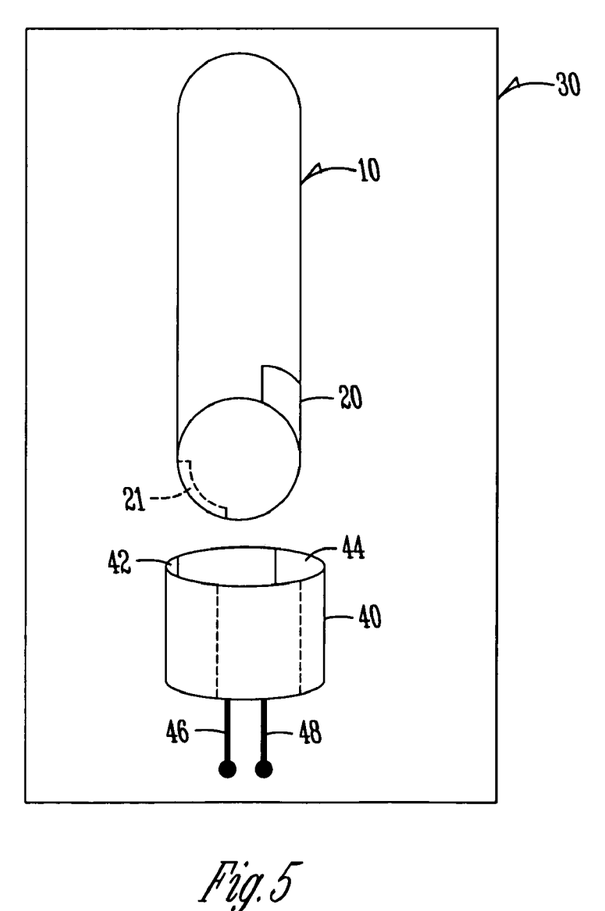
FIG. 5 is a perspective view of another embodiment of the present invention illustrating connection of a coil to a probe housing.

FIG. 5 illustrates one manner in which the coil 10 can be connected to the probe housing 30. As shown in FIG. 5, the coil 10 has a pad 20 and a pad 21. The probe housing 30 has a coil connector 40 that includes a first contact member 42 and a second contact member 44. The coil 10 can be press-fit into the probe connector 40 so that the pad area 20 of the coil 10 is in contact with the coil contact 44 and the pad 21 is in contact with the coil contact 42. The present invention contemplates that the coil 10 can engage with the coil connector 44 in various ways. It is preferred that the coil 10 be securely engaged with the connector 40. It is also preferred that the coil 10 be releasably engaged with the connector 40 to facilitate easy removal and replacement of the coil 10. Due to the reduced variability of the coil 10 of the present invention, the present invention contemplates that coils 10 can be interchanged. Lead wires 46 and 48 are also shown extending from the probe connector 40.

Figure 6:
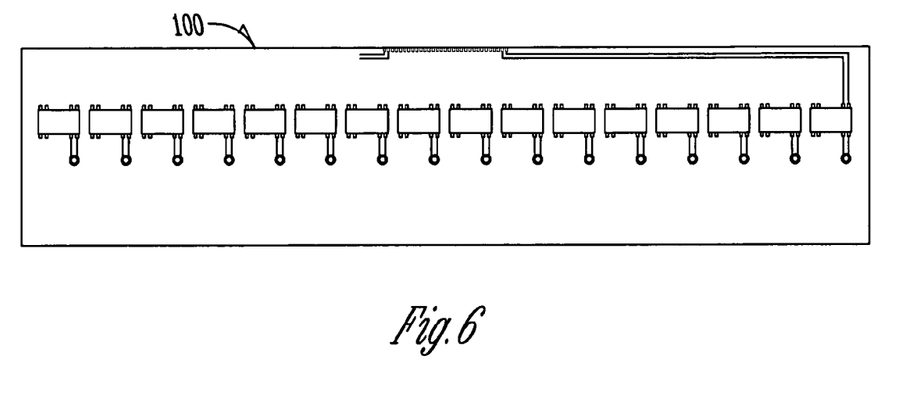
FIG. 6 is a partial view of one embodiment of a probe head for a sensor array showing the reverse side of the sensor where integrated circuits are used to amplifier signals from the individual sensors.
Figure 7:
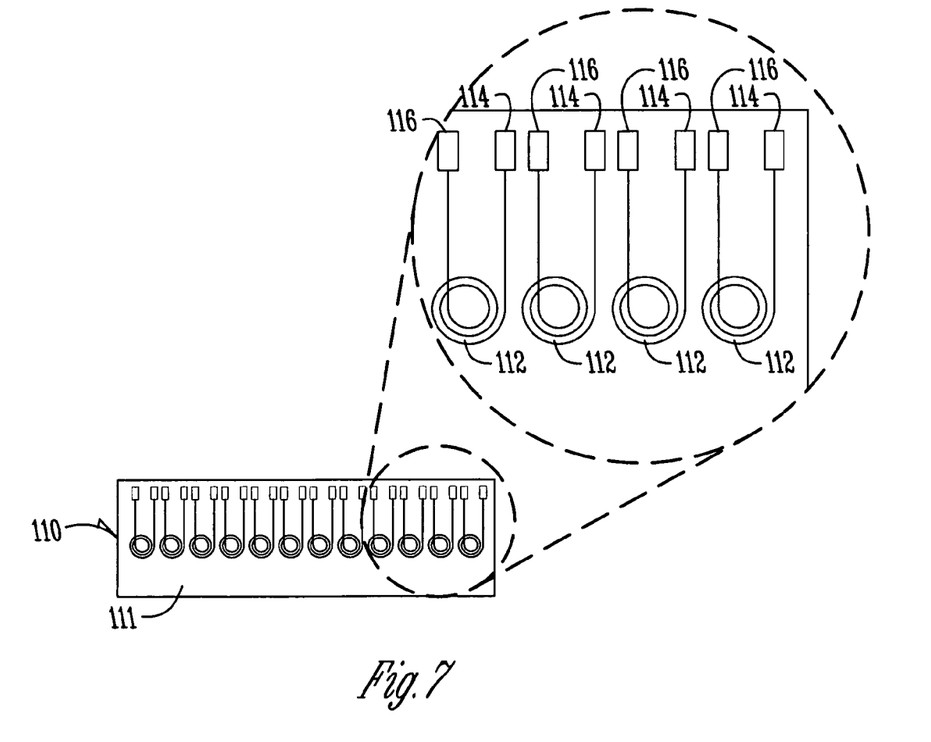
FIG. 7 is a view of one embodiment of a sensor array.

FIGS. 6 and 7 illustrate another embodiment of the present invention. In FIG. 7, a sensor array 110 is shown having a plurality of sensor elements 112. As shown in FIG. 6, a circuit board 100 includes circuitry such as amplifiers and buffers to maintain signal integrity. The circuit board 100 may be electrically connected to an existing multi-channel demodulator. The circuit board 100 is electrically connected to the sensor array 110.

The sensor array 110 has a substrate 111 such as KAPTON or other polyimide material that is flexible in nature. Each of the sensor elements 112 has terminals 114, 116 for electrically connecting each of the sensor elements 112 to the circuit board 100. Preferably, each of the sensor elements 112 or coils is directly written to the substrate 111. In operation, the sensor array 110 is scanned over a surface of a test specimen. The use of the sensor array 110 increases the rate at which analysis of a surface can be performed. It is further observed that due to the reduced variability of each coil, the calibration problems associated with a sensory array are reduced thereby making the use of a sensory array practical.

The present invention further contemplates that the sensor elements or coils 112 can be direct written onto other types of substrates in addition to polyimide. The substrate can be a molding associated with complex parts. In particular, in one embodiment of the present invention, sensor elements are positioned within molded forms designed to inspect parts having complex geometries. For example, the fir-tree slot in a jet engine could use a specially molded probe body that slides snugly up and down the slot. Such an embodiment of the present invention provides for positional reproducibility. The present invention allows a coil to be directly written onto the complex molding to thereby provide a significant advantage over a conventional approach of bonding a prior art coil into holes cut in the molding.

Figure 8:
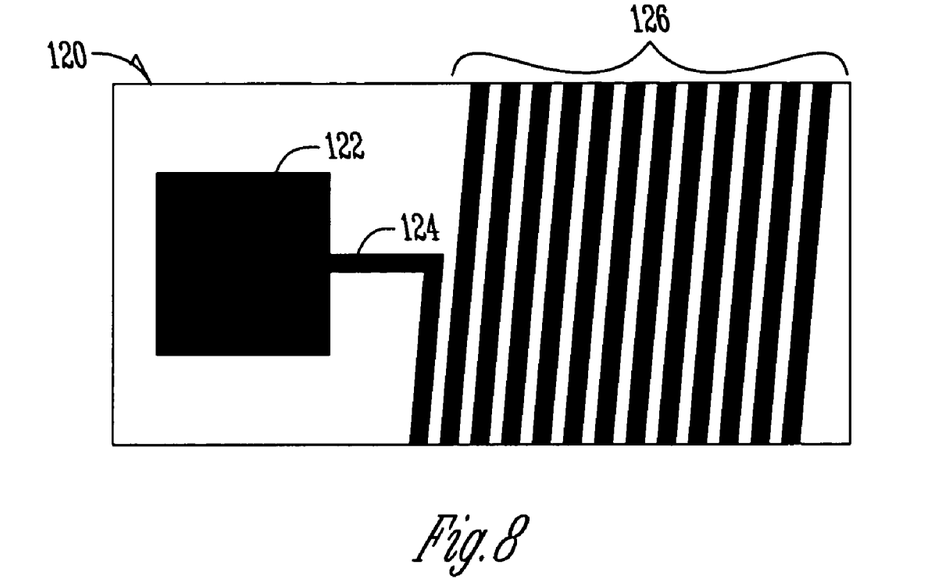
FIG. 8 is a side view of one embodiment of a coil of the present invention.
Figure 9:
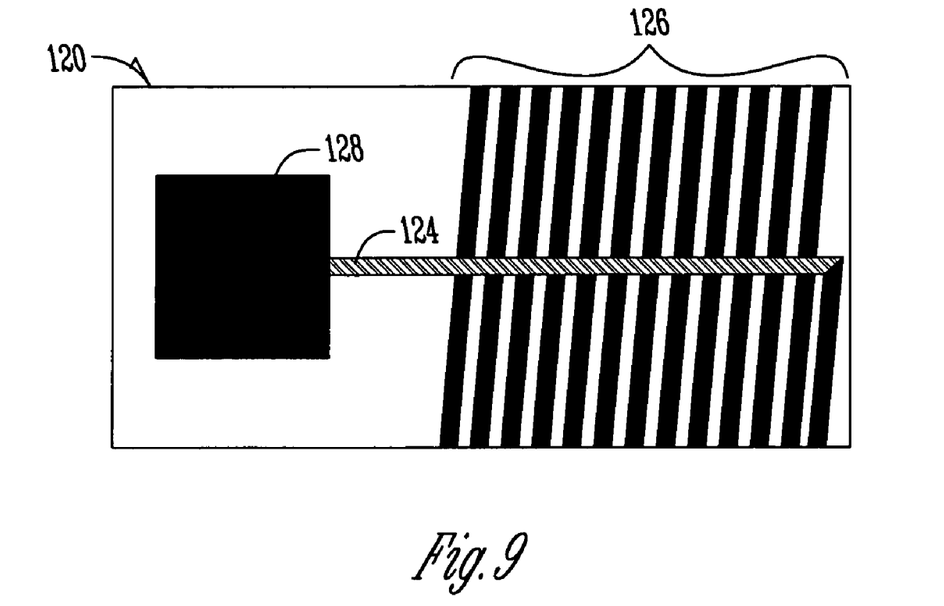
FIG. 9 is an opposite side view of one embodiment of a coil of the present invention.

FIGS. 8 and 9 illustrate another embodiment of a coil of the present invention, similar to the embodiment shown in FIG. 1. In FIG. 8, a coil device 120 has a large area contact pad 122 electrically connected through trace 124 to a winding 126. Preferably, the winding 126 is formed through a direct write procedure. The contact pad 122 is preferably a deep silver contact pad to ensure hard wearing and the contact pad 122 may be formed through a deposition procedure.

FIG. 9 shows an opposite side of the same coil 120 shown in FIG. 8. Note that a large area contact pad 128 is opposite the large area contact pad 122 of FIG. 8. In FIG. 9, a return track 124 is shown to provide a return track for the final winding. The return track 124 is electrically insulated from the winding 126.

Figure 10:
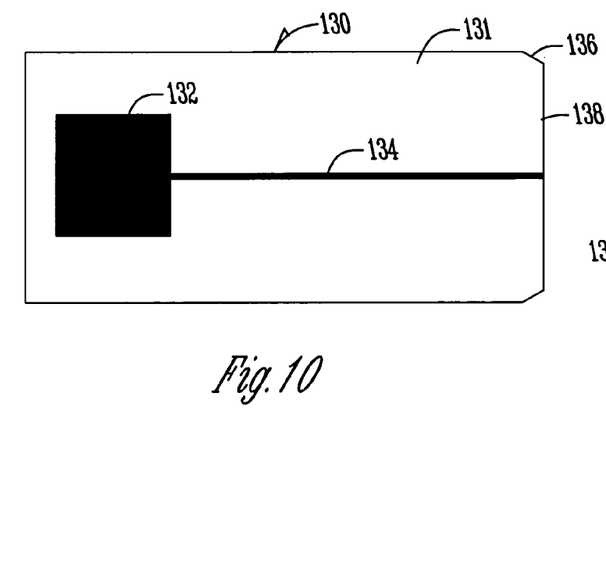
FIG. 10 illustrates a side view of one embodiment of a coil of the present invention where windings are deposited on the end of a ferrite coil.
Figure 11:
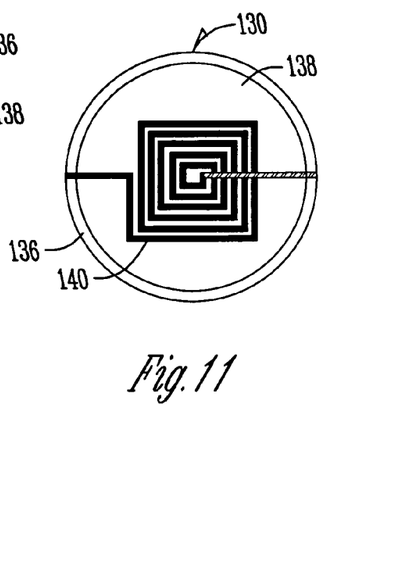
FIG. 11 is an end view of the embodiment of FIG. 10.

Another embodiment of the present invention allows one or more coils to be printed on the end of a core. Due to the precision that is afforded by the present invention, including, for example, the use of direct writing, windings of a coil can be deposited on the end of a core such as a ferrite rod. FIGS. 10 and 11 illustrate one such embodiment.

In FIG. 10, a coil device 130 for use in an eddy current sensor probe is shown including a ferrite rod as a core 131 having an end 138. The beveled edge 136 aids in the deposition procedure. A large area contact pad 132 is on either end of the coil device 130. Each contact pad is electrically connected to the windings through a track 134.

In FIG. 11, the end 138 of the core 131 is shown. Note the beveled edge 136 to aid in deposition. The windings 140 are deposited on the end 138 of the core 130 in a spiral or square spiral pattern as may be appropriate in a particular application. It should further be appreciated that the core 131 need not be cylindrical but can be of polyhedral shapes.

In one embodiment the end 138 of the core 131 has a diameter of approximately 0.0625 inches. The number of turns of the winding 140 is preferably at least 10. Of course, the present invention contemplates numerous variations in the number of turns of the winding 140 which will depend in part on the diameter of the core 131 and the thickness of traces used in the winding 140.

Figure 12:
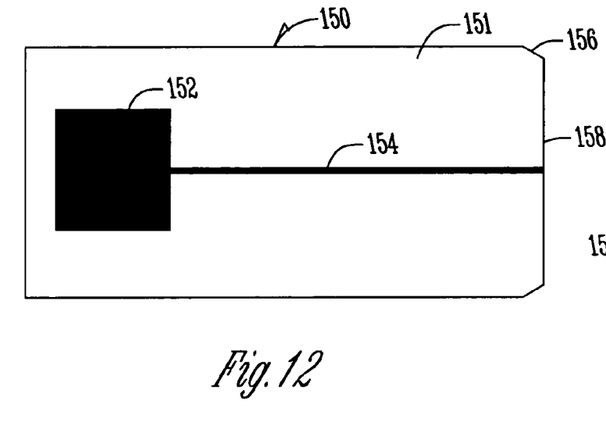
FIG. 12 is a side view of one embodiment of a coil of the present invention for a split-D (differential) coil on the end of a rod.

FIGS. 11 and 12 illustrate another embodiment of the present invention. In FIG. 11, a coil device 150 has large area contact pads 152 deposited on opposite sides (only one is shown) with a track 154 to a coil on the end 158 of the core 151. Note that the core 151 has a beveled edge 156 to aid in the deposition process.

Figure 13:
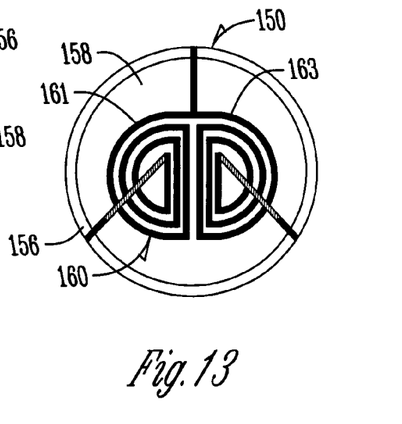
FIG. 13 is an end view of the embodiment of FIG. 12 of the split-D (differential) coil on the end of a rod.

In FIG. 12, the end 158 of the core 150 has deposited thereon a pattern 160 of two coils wound symmetrically in a split-D (differential) coil structure. Preferably, the pattern 160 has coils 161 and 163 of at least five turns. Note that the configuration shown in FIG. 13 has three paths extending from the end 158 to and along the side surface of the device one path for each of the coil patterns and one return track. The present invention contemplates that this or even more complex patterns may be used depending upon the particular application or use of the invention.

Figure 14:
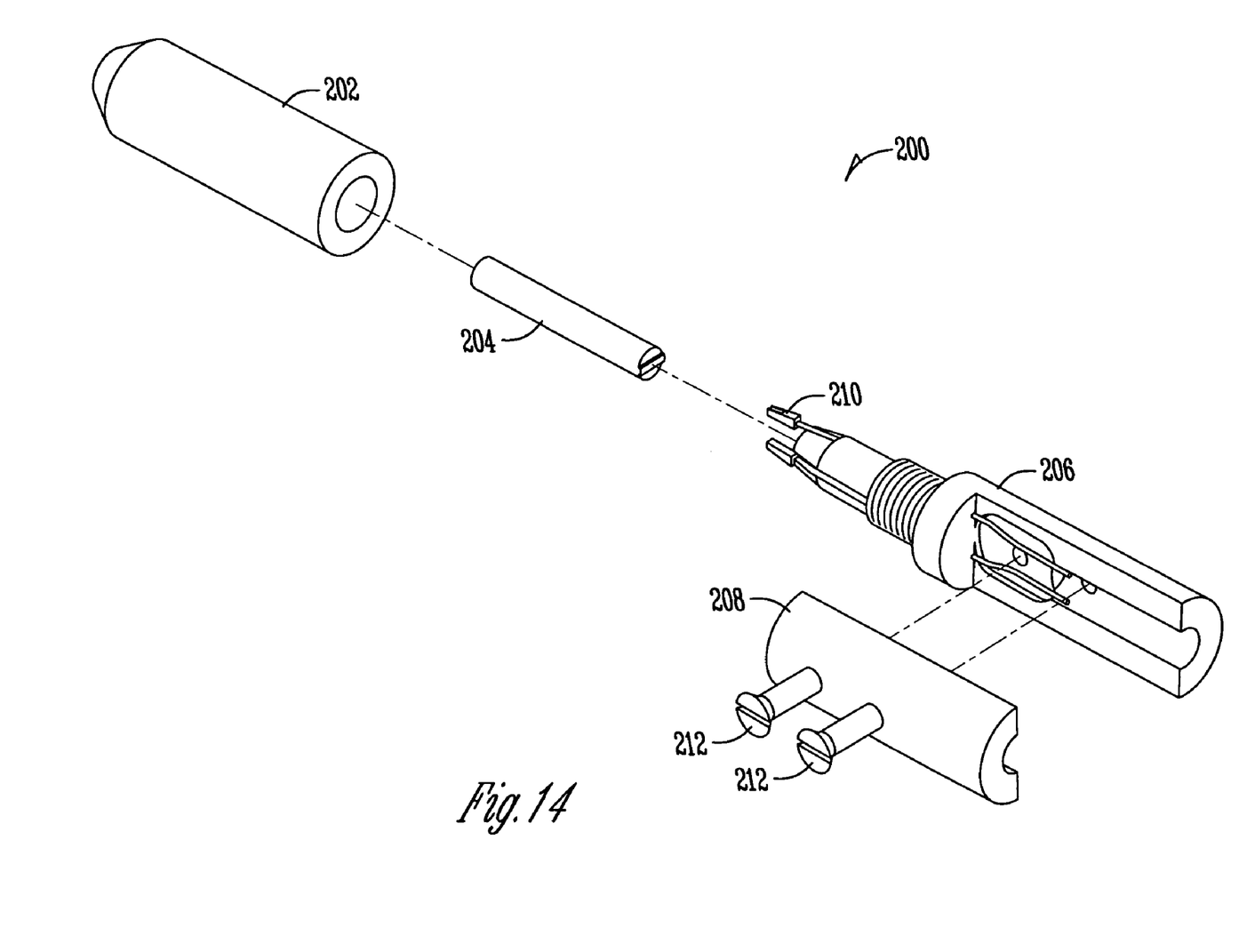
FIG. 14 is an exploded view of one embodiment of a coil of the present invention.
Figure 15:
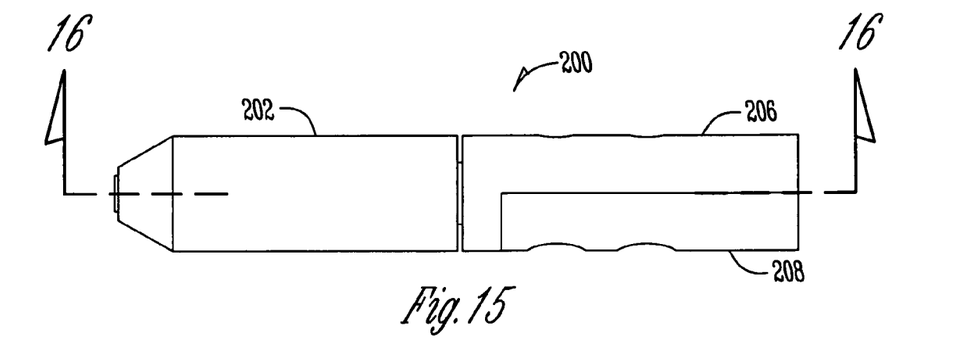
FIG. 15 is side view of of the coil shown in FIG. 14.
Figure 16:
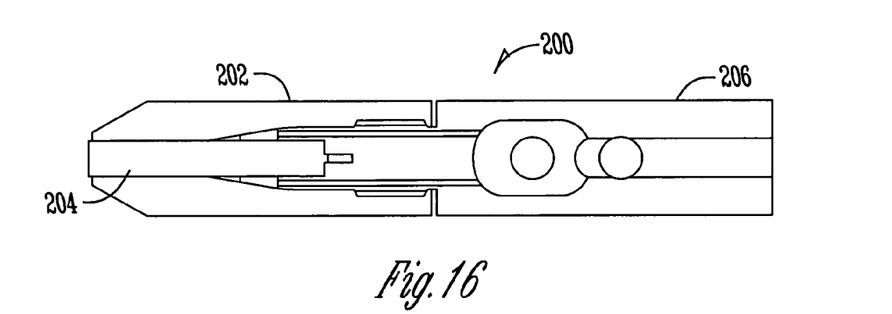
FIG. 16 is a sectional view of the coil shown in FIGS. 14 and 15.

FIGS. 14-16 illustrate another embodiment of the present invention. In FIGS. 14-16 a coil is shown. FIG. 14 is an exploded view of coil 200. A collet nut 202 is shown in relationship to a ferrite core 204. Although different sizes of parts may be used, one example of a diameter of the ferrite core 204 is 3 mm. A copper contact 210 is shown soldered to magnet wire. A collet or pen 206 is also shown as well as a cover or strain relief 208 for a triax cable (not shown) used to connect the coil 200 to the appropriate electronics. The cover 208 can be connected in various ways, including through the use of the screws 212. Instead of screws, a clamp, such as a nylon band clamp or other fastener can be used. FIG. 15 illustrates a side view of the coil 200 while FIG. 16 provides a sectional view showing the coil 200 as assembled. That which is shown in FIGS. 14-16 is merely one embodiment of a coil according to the present invention. It should be appreciated that the present invention contemplates numerous variations in the specific structure of the coil. It is further observed that the coil 200 of FIGS. 14-16 is generally pencil shaped in appearance but can be adapted to any number of shapes or configurations such as may be appropriate for a specific inspection process.

Figure 17:
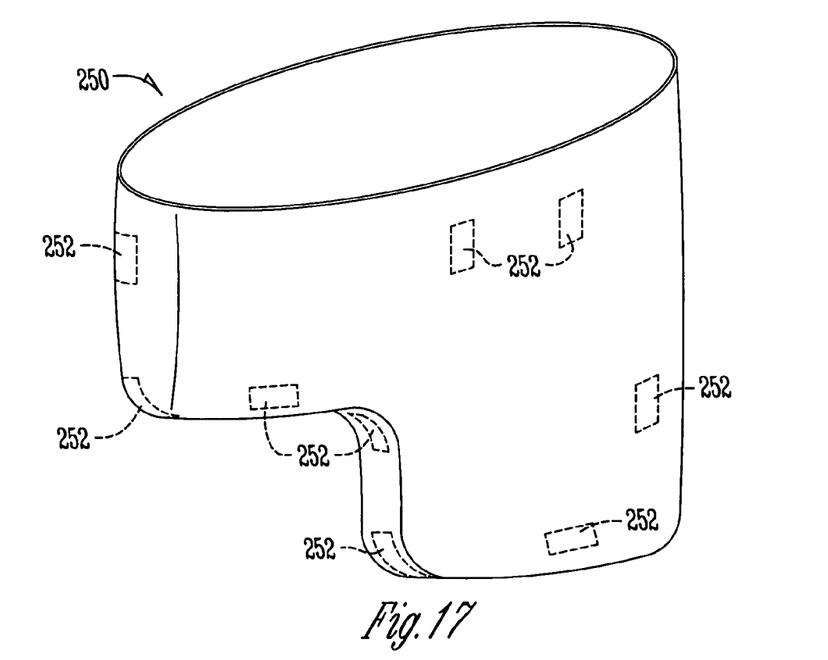
FIG. 17 is a diagram illustrating a coil on a molded body according to one embodiment of the present invention.

FIG. 17 illustrates another embodiment of the present invention. In FIG. 17, a molded body 250 is shown which is adapted to fit a particular inspection objection. The present invention contemplates that the molded body may be of any number of shapes, sizes, or configurations. Due to the use of the a direct write process the molded body 250 serving as the substrate (or underlying a substrate) can take on any of a number of shapes and a plurality of coils 252 are placed on the molded body in desired locations. Thus, the molded body 250 enables the inspection of complex parts. The desired locations can include locations typically associated with increased stresses or flaws. The use of the molded body provides for improved positional reproducibility to further increase the convenience and efficiency of an inspection and encourage the use of an increased number of inspection points. Note that the pads and electrical connections for each coil are not expressly shown, but would be positioned in a manner most convenient or otherwise appropriate for a particular application.

The present invention further provides for additional advantages from the ability to use film windings, and in particular the use of a direct write process. In one embodiment of the present invention, sensor elements are positioned within molded forms designed to inspect parts having complex geometries. For example, the fir-tree slot in a jet engine would use a specially molded probe body that slides snugly up and down the slot. Such an embodiment of the present invention provides for positional reproducibility. The present invention allows a coil to be directly written onto the complex molding to thereby provide a significant advantage over a conventional approach of bonding a prior art coil into holes cut in the molding.

Therefore, a method and apparatus for a coil for use in an eddy current sensing probe has been disclosed. The present invention contemplates variations in the number of layers of the coil, the types of materials used for the core body, the types of materials used for the winding, the process used to deposit the windings, the number of film windings, the width of the film winding, the number of turns in each winding, the number of layers, the manner in which the coil is connected to a probe housing, and other variations. All of these variations and other variations are well within the spirit and scope of the invention.

What is claimed is:

1. A coil for use in an eddy current sensing probe, comprising:
a core body having a first end and an opposite second end and an outer surface extending around the body;
a deposited film winding comprising a plurality of turns overlaying and directly attached to the core body, each of the plurality of turns extending annularly around the outer surface of the body to form an eddy current sensing coil;

wherein the outer surface of the core body is coated with a first insulative coating, wherein the first insulative coating provides a smooth surface;

a second insulative layer overlaying at least a portion of the film winding.

2. The coil of claim 1 wherein the body comprises ferrite.

3. The coil of claim 1 wherein the film winding is deposited by direct-writing.

4. The coil of claim 1 wherein the coating is a plastic coating.

5. The coil of claim 4 wherein the coating is a thermoplastic polymer coating.

6. The coil of claim 1 further comprising a film return track deposited on the second insulative layer, the return track electrically connected to a first end of the winding.

7. The coil of claim 6 further comprising a first pad and a second pad electrically connected to the winding, the second pad electrically connected to the return track.

8. An eddy current sensing probe, comprising:
a probe housing;
an eddy current coil disposed within the probe housing;
the eddy current coil comprising (a) a core body having a first end and an opposite second end and an outer surface extending around the core body, (b) a film winding comprising a plurality of turns deposited over the core body, (c) a pair of pads for electrically connecting to the ends of the film windings;
wherein the probe housing is adapted to securely engage the pads of the eddy current coil.

9. The eddy current sensing probe of claim 8 wherein the plurality of turns extend annularly around the body.

10. The eddy current sensing probe of claim 8 wherein the probe housing is adapted to securely engage the pads of the eddy current coil through a press fitting.

11. The eddy current sensing probe of claim 8 wherein the probe housing is adapted to releasably engage the pads of the eddy current coil, to facilitate removal and replacement of the eddy current coil.

12. The eddy current sensing probe of claim 8 wherein the plurality of turns are deposited on the first end of the core body.

13. An eddy current sensing probe, comprising:
a probe housing;
an eddy current coil disposed within the probe housing the eddy current coil comprising (a) a core body having a first end and an opposite second end and an outer surface extending around the core body, and (b) a film winding comprising a plurality of turns deposited over the core body;
wherein the film winding is patterned to form a first coil pattern and a second coil pattern positioned on the first end of the core body.

14. The eddy current sensing probe of claim 13 wherein the first coil pattern and the second coil pattern are configured in a differential configuration.

15. An eddy current sensing probe, comprising:
an eddy current coil disposed within the probe housing;
the eddy current coil comprising
(a) a core body having a first end on opposite second end and an outer surface extending around the core body, and
(b) a film winding comprising a plurality of turns deposited over the body; and
a return trace deposited on the core body.

* * * * *